US011992358B2

(12) United States Patent
Singhrao et al.

(10) Patent No.: US 11,992,358 B2
(45) Date of Patent: May 28, 2024

(54) MULTIMODALITY ANTHROPOMORHIC PHANTOM APPARATUS

(71) Applicant: The Regents of the University of California, Oakland, CA (US)

(72) Inventors: Kamal Singhrao, Los Angeles, LA (US); John H. Lewis, Pacific Palisades, CA (US)

(73) Assignee: The Regents of the University of California, Oakland, CA (US)

( * ) Notice: Subject to any disclaimer, the term of this patent is extended or adjusted under 35 U.S.C. 154(b) by 349 days.

(21) Appl. No.: 17/429,190

(22) PCT Filed: Feb. 13, 2020

(86) PCT No.: PCT/US2020/018076
§ 371 (c)(1),
(2) Date: Aug. 6, 2021

(87) PCT Pub. No.: WO2020/168054
PCT Pub. Date: Aug. 20, 2020

(65) Prior Publication Data
US 2022/0139262 A1     May 5, 2022

Related U.S. Application Data

(60) Provisional application No. 62/846,141, filed on May 10, 2019, provisional application No. 62/804,858, filed on Feb. 13, 2019.

(51) Int. Cl.
*A61B 6/58* (2024.01)
*G01R 33/58* (2006.01)
*G09B 23/28* (2006.01)

(52) U.S. Cl.
CPC .............. *A61B 6/583* (2013.01); *G01R 33/58* (2013.01); *G09B 23/286* (2013.01)

(58) Field of Classification Search
CPC ....... A61B 6/583; G01R 33/58; G09B 23/286
See application file for complete search history.

(56) References Cited

U.S. PATENT DOCUMENTS

| 5,547,656 A | 8/1996 | Unger |
| 2006/0027756 A1 | 2/2006 | Thomson et al. |

(Continued)

FOREIGN PATENT DOCUMENTS

CN     108523917 A     9/2018

OTHER PUBLICATIONS

Bojorquez, J.Z., et al., "What are normal relaxation times of tissues at 3 T?", Magn. Reson. Imaging 35 (2017), 69-80.

(Continued)

*Primary Examiner* — Chih-Cheng Kao
(74) *Attorney, Agent, or Firm* — Quarles & Brady LLP

(57) ABSTRACT

A multimodality phantom apparatus includes a housing and a system of materials disposed within the housing. The system of material includes a first amount of abase material, a second amount of glass microspheres, a third amount of CaCO3, a fourth amount of gadolinium contrast and a fifth amount of agarose. The housing may include a plurality of compartments and at least one slot. The system of materials may be disposed within at least one compartment. The slot may be used to receive a dosimeter.

20 Claims, 9 Drawing Sheets

(56) References Cited

U.S. PATENT DOCUMENTS

| | | | | |
|---|---|---|---|---|
| 2013/0089186 A1* | 4/2013 | Payne | ............... | A61B 6/583 |
| | | | | 378/207 |
| 2016/0027340 A1* | 1/2016 | Chiribiri | ............... | A61B 6/583 |
| | | | | 434/268 |
| 2016/0089106 A1* | 3/2016 | Kirby | ............... | A61B 6/58 |
| | | | | 378/207 |
| 2017/0347987 A1* | 12/2017 | Hong | ............... | A61B 6/583 |

OTHER PUBLICATIONS

D'Souza, WD., et al., "Tissue Mimicking Materials for a Multi-Imaging Modality Prostate Phantom", Medical Physics, vol. 28, No. 4, Apr. 2001, 688-700.

Hattori, K., et al., "Development of MRI Phantom Equivalent to Human Tissues for 3.0-T MRI", Med. Phys., 40(3), Mar. 2013, pp. 032303-1-032303-11.

Niebuhr, N.I., et al., "Technical Note: Radiological properties of tissue surrogates used in a multimodality deformable pelvic phantom for MR-guided radiotherapy", Med. Phys. (2016) 43(2) 908-916.

Singhrao, K., et al., "A three-dimensional head- and-neck phantom for validation of multimodality deformable image registration for adaptive radiotherapy", Med. Phys. (2014) 41(12):121709-1-121709-7.

Book of Abstracts, ESMRMB 2005, 22nd Annual Scientific Meeting, Sep. 15-18, 2005, EPOS Posters, pp. S176-S306.

European Patent Office, Extended Search Report, Application No. 20755647.3, dated Sep. 13, 2022, 9 pages.

* cited by examiner

MULTIMODALITY ANTHROPOMORHIC PHANTOM APPARATUS

CROSS-REFERENCE TO RELATED APPLICATIONS

The present application represents the national stage entry of International Application No. PCT/US2020/018076, filed Feb. 13, 2020, which is based on, claims priority to, and incorporates herein by reference in its entirety U.S. Ser. No. 62/804,858 filed Feb. 13, 2019 and entitled "Multimodality Phantom Apparatus" and U.S. Ser. No. 62/846,141 filed May 10, 2019 and entitled "Multimodality Anthropomorphic Physical Phantom For MRI-Based Radiotherapy and Medical Imaging."

BACKGROUND

Magnetic Resonance (MR) and Computer Tomography (CT) imaging are two of the most commonly used three-dimensional (3D) medical imaging tools. Many groups of patients such as brain and prostate cancer patients typically receive both MR and CT imaging for diagnostic and radiation treatment planning purposes. Typically, MR and CT imaging machines would be calibrated and quality assurance-tested separately for their respective applications using specialized phantoms (instruments for imaging or radiation dose measurements) capable of producing contrast on their respective modalities. The advent of applications such as MR-guided radiation therapy and MR-only radiation treatment planning has led to the need for materials and phantoms that are capable of producing contrast for bone and soft-tissue on both MR and CT imaging modalities. The development of tissue mimicking materials for both MR and CT is challenging because it requires matching the electron density or x-ray attenuation and local magnetic field properties of human tissue. Additionally, there are practical challenges to creating multimodal tissue mimicking materials such as their longevity, castability, stability, deformability and ease of production.

Producing a tissue surrogate material for multimodal MR and CT imaging requires it to have similar X-ray scattering and nuclear magnetic resonance behavior of different human tissues. Protons are the source of contrast-producing signals in MR imaging. After a large external magnetic field is applied, the protons align parallel or anti-parallel to the external magnetic field. Upon application of a gradient field, the proton spins are knocked off axis and then slowly realign with the external magnetic field. The time the proton takes to realign with the external magnetic field can be characterized as the $T_1$ and $T_2$ relaxation time constants. $T_1$ and $T_2$ relaxation times determine the time the proton spin vector takes to realign with the external magnetic field in the longitudinal and transverse directions respectively. $T_1$ and $T_2$ relaxation times depend on the molecular tumbling rate of individual tissues. Contrast in CT is produced by the ability of X-rays to traverse through different tissue types. The more radiopaque a tissue is, the less likely X-rays will be able to traverse through it without large angle scattering. X-rays traverse from a source, through a patient and are detected by an array of scintillators, photodiodes, and pixel electronics. Radiopacity is described using the Hounsfield Unit (HU) scale. A HU (or CT number) of −1000 HU represents air, −120 HU represents fat, 0 HU represents water, 20-200 HU represents most soft tissues and greater than 700 HU represents bone.

Current work on the development of multimodal materials (suitable MR-CT materials) has been limited because of the difficulty in reproducing MR imaging characteristics for a wide range of tissues. D'Souza et al. (W. D. D'Souza, E. L. Madsen, O. Unal, K. K. Vigen, G. R. Frank, and B. R. Thomadsen, Med. Phys. 28, 688 (2001)) developed a tissue mimicking prostate phantom for multimodal imaging. Prostate and muscle tissue contrast was developed using water, agarose, lipid particles, condensed milk, $CuSO_4$. EDTA and glass beads, with thermiserol as a preservative. Adipose tissues were mimicked using safflower oil in a polyurethane mesh. $T_1$ and $T_2$ relaxometry was performed on a 0.94T 40 MHz relaxometer. This phantom was able to mimic soft tissue behavior well for prostate, skeletal muscle and adipose tissue at 0.94T. However, there are several limitations to this system of materials. MR relaxometry for this system of materials has not been tested at higher fields. The use of animal tissue may hinder reproducibility and may be subject to long term degradation. This system of materials also cannot mimic the MR characteristics of different types of adipose tissue such as glandular breast tissue. Niebuhr et al. (N. I. Niebuhr, W. Johnen, T. Güldaglar, A. Runz, G. Echner, P. Mann, C. Mohler, A. Pfaffenberger, O. Jakel, and S. Greilich, Med. Phys. 43, 908 (2016)) created tissue surrogate materials using agarose gels, gadolinium and NaF to mimic muscle and soft tissues, and olive oil to mimic adipose tissue. MR relaxometry was performed on a 1.5T MR system and CT images were acquired on a dual source CT system. This approach allowed for the development of generalized fits to mimic a range of soft tissues using gadolinium, agarose and NaF. However, this approach was limited because the use of large amounts of NaF salts caused the formation of severe artifacts in MR images such as $T_2$-weighted images. Additionally, the use of olive oil to mimic adipose tissue does not allow generalizability to other types of human adipose tissue. Polyvinyl chloride (PVC)-based materials have also been developed as a multimodal tissue-mimicking material. Tissue surrogate materials were created by varying the PVC-softener ratios and, the mass fractions of mineral oil and glass microspheres in PVC. The CT numbers for this system of PVC-based materials varied from −10 to 110 HU. The measured $T_1$ and $T_2$ relaxation times were 206.81±17.50 and 20.22±5.74 ms, respectively. The PVC-based system of materials can only mimic the CT numbers of non-adipose tissue based soft tissues. Additionally, the $T_1$ and $T_2$ relaxation times do not appear to be variable thereby limiting this system of materials use for MR-guided calibration instruments.

Carrageenan based materials have been developed to mimic a diverse array of soft tissues. Hattori et al. (Hattori Kengo, Ikemoto Yusuke, Takao Wataru, Ohno Seiichiro, Harimoto Takashi, Kanazawa Susumu, Oita Masataka, Shibuya Koichi, Kuroda Masahiro, and Kato Hirokazu, Med. Phys. 40, 32303 (2013)) developed the Carrageenan-Agarose-Gadolinium-NaCl (CAGN) phantom for 3.0T MR imaging. The CAGN phantom used carrageenan as a gelatinizer, and gadolinium and agarose to control $T_1$ and $T_2$ relaxometry. The CAGN phantom was able to mimic $T_1$ and $T_2$ relaxometry for most soft tissues such as muscle, gray matter and cervix at 3.0T fields. This method uses a base material with long $T_1$ and $T_2$ relaxation times, which allows the MR characteristics to be easily tuned using $T_1$ and $T_2$ altering agents. For CT imaging, Singhrao et al. (K. Singhrao, N. Kirby, and J. Pouliot, Med. Phys. 41, n/a (2014)) used glass microspheres to decrease and calcium carbonate power to increase the CT number (or Hounsfield Unit (HU) number) of a cast polyurethane mold.

The use of MR in radiotherapy is becoming increasingly prevalent because MR imaging provides excellent soft tissue visualization. Examples of the utilization of MR imaging in clinical practice include registration of planning CT and MR imaging for target delineation, treatment using MR-guided treatment units, and MR-only simulation and treatment planning. Quality assurance (QA) testing equipment requirements for MR-based radiotherapy are different than those for standard CT-based workflows. Several types of QA are performed in the current CT imaging workflow including end-to-end testing, daily treatment verification QA, monthly and annual QA. Most QA tests use objects, called phantoms, which serve as proxies for human tissues or water for radiation dosimetry measurements. End-to-end QA testing is typically performed on new radiotherapy machines prior to the first patient treatments, and after any major equipment or software changes. End-to-end QA is designed to test the entire treatment process including treatment simulation, planning and delivery. Daily, monthly and annual QA include periodic radiation dosimetry tests performed using ion chamber, film, or thermoluminescent dosimeter (TLD) measurements to verify RT machine output. The phantoms used for QA typically have similar x-ray attenuation properties to water or human tissues, and can contain anthropomorphic features to mimic the x-ray scattering properties human tissues and inserts or adaptors for dosimetry measurements As the use of MR imaging in radiotherapy continues to grow rapidly, there is an increasing need for equipment well-suited to the development, evaluation, and quality assurance of MR-based radiotherapy workflows. Phantoms play a critical role in acceptance, commissioning, and periodic quality assurance (QA) of, for example, linear accelerators (linacs) and imaging systems, and standardizing multisite clinical trial design. Phantoms capable of providing human tissue-like images on CT and a variety of MR imaging sequences are required to be able to directly compare new or existing MR-based workflows with current CT-based clinical processes. However, most commonly available phantoms do not mimic both MR and CT tissue imaging characteristics for different human organs making it challenging to comprehensively test MR-based processes such as synthetic CT (sCT) image generation.

The introduction of MR-based treatments has resulted in a number of challenges when attempting to use QA devices optimized for the CT-based workflows. The presence of a strong magnetic field prevents any non-MR-safe phantom (containing ferromagnetic materials) from being used for MR-based radiotherapy QA. Treatment planning QA requires the definition of a treatment target in the phantom requiring a tissue-like target. Using materials with good MR-CT characteristics allows new MR-based radiotherapy plans to be directly compared to the current CT-only gold standard. Additionally, verification of MR-based dose calculation methods requires phantoms to mimic human tissue. Dose calculations using MR-based treatments such as MR-only simulation with x-ray image guided radiotherapy (IGRT) typically require synthetic CT (sCT) generation because of the lack of electron density information in MR images. The clinical QA process for sCT evaluation is not well defined. However, there is potential for physical phantom-based QA to verify the quality of sCT and compare them to their CT-based ground truth counterparts. This requires a phantom with excellent MR and CT imaging characteristics because sCT algorithms are highly sensitive to non-anthropomorphic structures such as the ones currently used in CT-only workflows.

Research in the development of phantoms for MR-based radiotherapy has helped determine promising potential component materials but has not yet lead to a practical solution suitable for widespread clinical use. Most commercially available MR phantoms produce MR contrast but do not have good $T_1$ and $T_2$ relaxation time matching to soft tissue. This limits their applicability for MR-based radiotherapy QA because of their inability to create realistic tissue contrast. Research phantoms have been developed that are designed to test MR-based radiotherapy workflows. However, the system of materials used in such phantoms are subject to MR-distortions making them difficult for MR contouring and sCT evaluation. Additionally, their structures do not allow for simple placement of radiation measurement devices such as ion chambers or radiochromic film for dose measurement and verification.

It would be desirable to provide a system of materials configured to be compatible with CT and MR imaging and to produce tissue-like contrast for both CT and MR imaging. In addition, it would be desirable to provide an anthropomorphic phantom that includes the system of materials and is capable of $T_1$, $T_2$, and electron density matching for bone and soft tissues.

SUMMARY OF THE DISCLOSURE

In accordance with an embodiment, a multimodality phantom apparatus includes a housing and a system of materials disposed within the housing. The system of materials includes a first amount of a base material, a second amount of glass microspheres, a third amount of $CaCO_3$, a fourth amount of gadolinium contrast and a fifth amount of agarose.

In accordance with another embodiment, a multimodality phantom includes a housing having a plurality of compartments and at least one slot. The slot may be used to receive a dosimeter. The multimodality phantom further includes a system of materials disposed within at least one compartment in the plurality of compartments. The system of materials includes a first amount of a base material, a second amount of glass microspheres, a third amount of $CaCO_3$, a fourth amount of gadolinium contrast and a fifth amount of agarose.

DETAILED DESCRIPTION

Figure 1A:
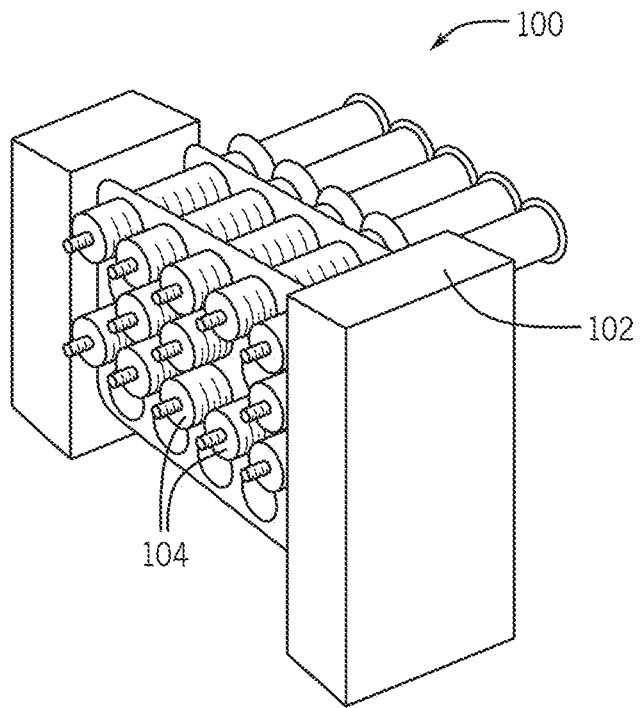
FIG. 1a shows exemplary tissue validation phantom with samples in accordance with an embodiment.

The present disclosure describes a system of materials capable of mimicking bone and a wide range of tissues, for example, adipose tissue, skeletal muscle and bone marrow, for MR (e.g., 0.35T to 3T) and CT imaging. The system of materials may be easily made and formed with adjustable $T_1$ and $T_2$ relaxation times, and x-ray attenuation properties (e.g., CT number) for mimicking soft tissues and bone. In an embodiment, the system of materials is a system of additive-doped carrageenan-based tissue mimicking materials. The present disclosure also describes a multimodality phantom that is created using the disclosed system of materials. In an embodiment, the system of materials is used to create a realistic, anthropomorphic phantom for MR and CT imaging. The multimodality phantom may be constructed to represent any anatomical site of the human body. The system of materials may be formed to create any organ shape. In an embodiment, a housing for the multimodality phantom is created using 3D-printing. The multimodality phantom may be used for various applications such as, for example, MR-based radiotherapy treatment quality assurance (QA) testing (e.g., end-to-end testing an MR-only treatment simulation and planning workflow), imaging calibration for MR and CT based radiotherapy treatments, dose measurement and positioning verification for MR and CT based radiotherapy treatments, evaluation of methods used to generate synthetic CT (sCT) images, general MR/CT imaging applications, verifying MR-CT image registration, testing and validation of MR-based radiotherapy processes (or workflows) by comparison with standard CT-based radiotherapy processes, benchmarking multisite MR-based clinical trials, and low field application such as calibrating MR sequences at low fields. Several advantages of the disclosed multimodality phantom (with the disclosed system of materials) are that the phantom is simpler to fabricate compared to previously known phantoms, the phantom produces realistic anthropomorphic CT images and $T_1$- and $T_2$-weighted MR images at a wide range og magnetic fields, and the phantom may be used to produce realistic sCT images using known sCT generation methods.

As mentioned, the disclosed system of materials is capable of producing tissue-like contrast in MR and CT imaging modalities. In one embodiment, the system of materials consists of a base material such as a carrageenan based gelatinizer as well as additives used to control CT number and $T_1$ and $T_2$ relaxation times. Carrageenan has several advantages when used as the base material (or gelatinizer) in the system of materials including that it produces a solid-at-room temperature gel and has minimal effects on $T_1$ and $T_2$ values. The additives include gadolinium (Gd) contrast to control $T_1$ behavior, agarose (Ag) to control $T_2$ behavior, and glass microspheres (GMs) and $CaCO_3$ to control the electron density (a CT number modifier). The glass microspheres may be pretreated with oil to mimic adipose tissue. The carrageenan-based system of materials does not exhibit shadowing artifacts which allows the generation of relatively artifact-free $T_1$- and $T_2$-weighted MR images. In other embodiments, other forms of a base material may be used such as a silicone-based material to which the additives may be introduced. The system of materials was designed to be easily made and formed with adjustable $T_1$ and $T_2$ relaxation times and x-ray attenuation properties for mimicking soft tissue and bone in both CT and MR imaging. In an embodiment, the system of materials are configured to be solid at room temperature and to liquefy at a higher temperature (e.g., 45° C.) which allows the system of materials to be formed into shapes. As discussed further below, the system of materials may be formed to create any organ shape.

In one example, a carrageenan-based system of materials was evaluated using a plurality of samples to determine the attainable ranges of $T_1$, $T_2$, and CT number (HU) combinations. In this example, the ranges of achievable CT numbers and $T_1$ and $T_2$ relaxation times included creating multiple phantom samples (i.e., carrageenan-based gels) with varying concentrations of four additives and performing CT number and $T_1$ and $T_2$ relaxometry measurements. The plurality of samples were constructed using carrageenan as a gelatinizer, Gd contrast agent (gadofosveset trisodium) as a $T_1$ modifier, agarose (e.g., A1700 Agarose LE powder) as a $T_2$ modifier, $CaCO_3$ as a CT number (HU) modifier (e.g., a CT number enhancer) and glass microspheres as a CT number modifier (e.g., a CT number diminisher) and deionized water. Gd contrast has a significant effect on decreasing $T_1$ relaxation time, agarose has the ability to modify $T_2$, $CaCO_3$ has been shown to increase CT number values, and glass microspheres have been shown to decrease CT number values.

In this example, the range of achievable CT and MR imaging tissue properties (CT number, $T_1$ relaxation time, $T_2$ relaxation time) was quantified by creating 50 g weight gel samples contained in syringes. Each sample had a fixed concentration of carrageenan at 3 w/w %. Over 100 samples (e.g., 110 samples) were made with different combinations of $T_1$, $T_2$ and CT number modifiers. Concentrations of Gd contrast were ranged from 0 to 500 μmol/kg, for example, at 0, 0.25, 2.5, 12.5 and 25 μmol/kg increments. Agarose concentrations ranged from 0 to 8 w/w %, for example, at 0, 2, 5 and 8 w/w % increments. $CaCO_3$ concentrations were varied from 0 to 50 w/w %, for example, 0, 5, 10, 20, 30 and 50 w/w % increments, and glass microspheres concentrations were varied from 0 to 10 w/w %, for example at 0, 5 and 10 w/w % increments. Samples were prepared in 100 ml borosilicate glass beakers. An initial base mix (e.g., 500 ml) of water and, if necessary, $CaCO_3$ and glass microspheres was prepared. A 50 g sample was prepared by adding agarose and/or Gd contrast to the base mix. For example, the base mix was poured into 100 ml beakers and agarose and/or Gd contrast was added if necessary. The gelling agents, carrageenan and agarose, were added last to prevent the samples from congealing. Each sample was kept on a hotplate to prevent solidification during construction. A sample was completed by funneling 50 g of the base mix into a 60 cc Leur Lock syringe and capped. The samples cooled to room temperature and stored.

Figure 1B:
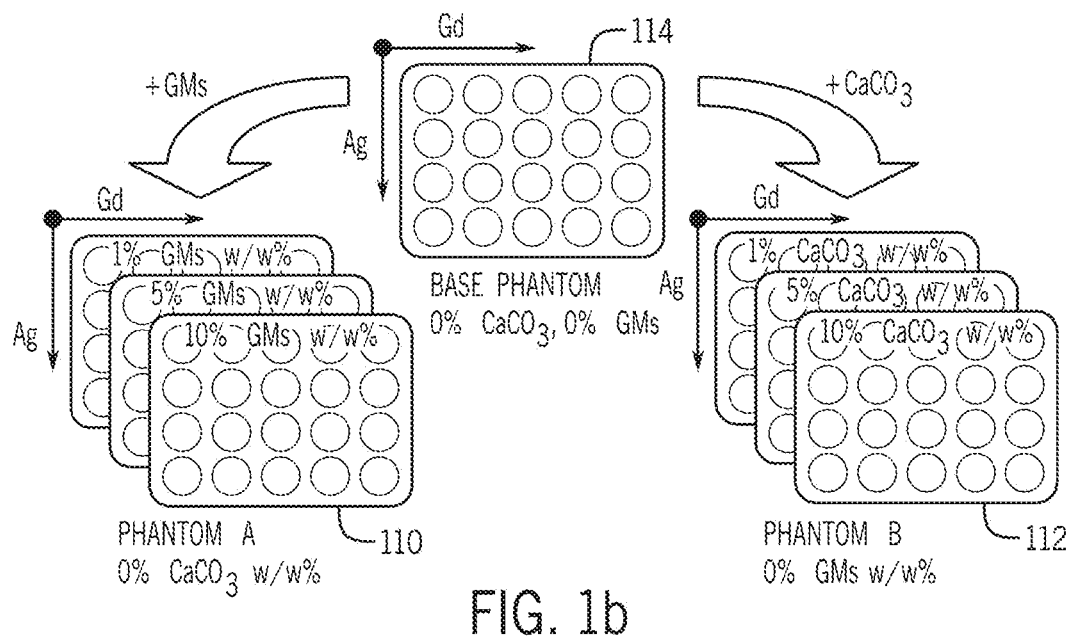
FIG. 1b is a diagram of an exemplary sample positioning in a tissue validation phantom in accordance with an embodiment.

In this example, the samples were tested to determine the relationship between $T_1$, $T_2$ and CT number values with respect to agarose, Gd contrast, glass microspheres and $CaCO_3$ concentrations. Sample syringes were placed in a tissue validation phantom, for example, a custom-made case designed to hold samples as shown in FIGS. 1a and 1b. FIG. 1a shows an exemplary tissue validation phantom 100 with samples 104. In one embodiment, the structure of the case 102 is created using 3D-printing. The tissue validation phantom 100 is configured to hold 20 samples 104 in a 4×5 grid. FIG. 1b is a diagram of an exemplary sample positioning in a a tissue validation phantom. In FIG. 1b, each validation phantom (Phantom A 110 and Phantom B 112) contains samples with fixed $CaCO_3$ or GM concentrations. Each phantom 110 and 112 was based on a base phantom 114 containing 20 samples with a range of Gd contrast and agarose concentrations. Samples were placed in the case of the tissue validation phantom such that the x and y axes represented increasing concentrations of Gd contrast and agarose respectively. The phantoms 110 and 112 were created with the same concentration variation of Ag and Gd as the base phantom 114 but with increasing concentrations of $CaCO_3$ (phantom 112) or GM concentrations (phantom 110). $T_1$ and $T_2$ measurements were performed on an MR system and CT images were acquired on a CT system. In this example, the MR system was a 3T MR system.

Figure 2:
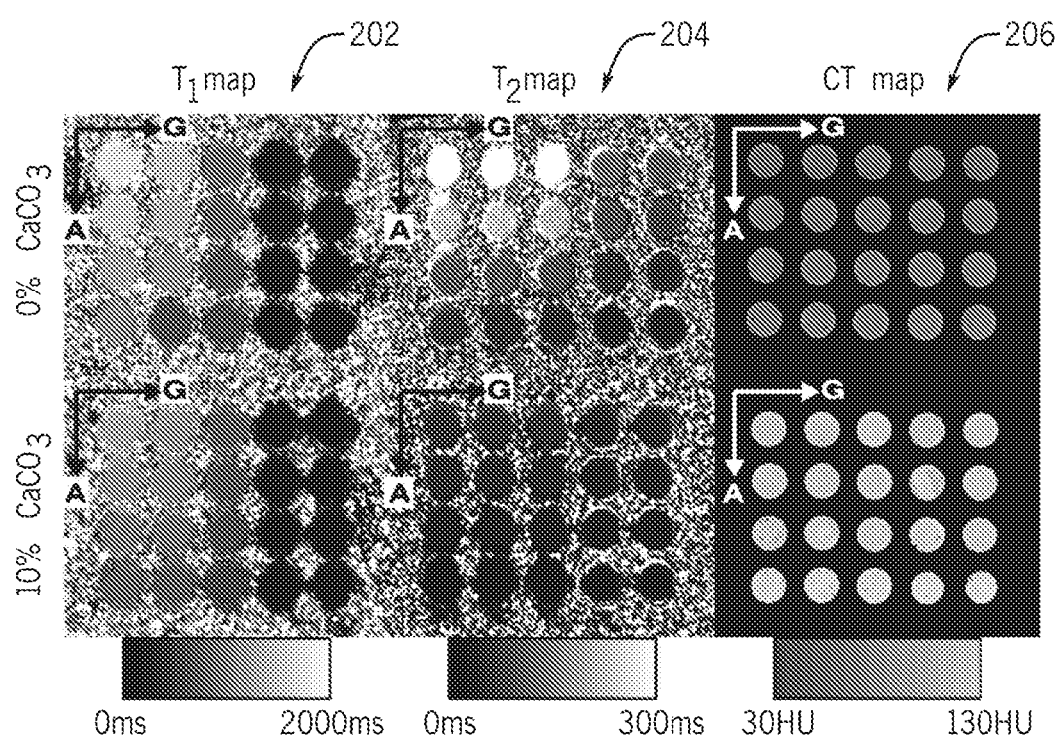
FIG. 2 shows example $T_1$ maps 202 and $T_2$ maps 204, and CT images 206 of phantom samples containing 0% and 10% $CaCO_3$ by weight.

As mentioned above, in this example the imaging properties of each sample were quantified using CT number and $T_1$ and $T_2$ relaxometry measurements. $T_1$ and $T_2$ relaxation times, and CT number for each sample were calculated within a 20 mm diameter region of interest inside each sample. In this example, a 3 millimolar $NiCl_2$ hexahydrate solution was used as a control. FIG. 2 shows example $T_1$ maps 202 and $T_2$ maps 204, and CT images 206 of phantom samples containing 0% and 10% $CaCO_3$ by weight. In FIG. 2, for reference the concentration axes of Gd contrast and agarose are indicated where the Gd concentration increases from left to right and the agarose concentration increases from top to bottom. $T_1$ measurements were acquired using an inversion recovery turbo spin echo (TSE) sequence with 180-degree refocusing pulses. The echo time (TE) and repetition time (TR) were fixed at 12 ms and 15,000 ms respectively, and the inversion time (TI) was varied from 25 ms to 2000 ms in 50 ms steps. Images were acquired using an echo train length of 22, no signal averaging and without parallel imaging. A 128×128 matrix, single 8 mm slice with a readout bandwidth of 130 Hz/px was acquired. A $T_1$ map was generated by performing a voxel-wise fit to the observed signal intensity using:

$$M_{z,TE_i} = M_0(1 - 2e^{-TI/T_1} - e^{-TR/T_1}) \quad (1)$$

where $M_0$ is the initial magnetization vector magnitude. $T_2$ measurements were acquired using spin echo images using a TSE sequence with a constant TR at 4000 ms and TE values 25, 50, 62, 75, 87, 107, 167, and 262 ms. Images were acquired with an echo train length of 25, 2 signal averages and without parallel imaging. $T_2$ maps were generated by performing a voxel-wise fit using:

$$M_{TE_i} = M_0 \left( e^{\frac{TE_i}{T_2}} \right) + c \quad (2)$$

where c is a noise offset variable. CT images were acquired with scanner settings at 120 kVp and 400 mAs. CT number was used as a surrogate for x-ray attenuation. CT images were acquired on a 20-slice single source CT system. All measurements were performed between 20° C. and 22° C.

Figure 3:
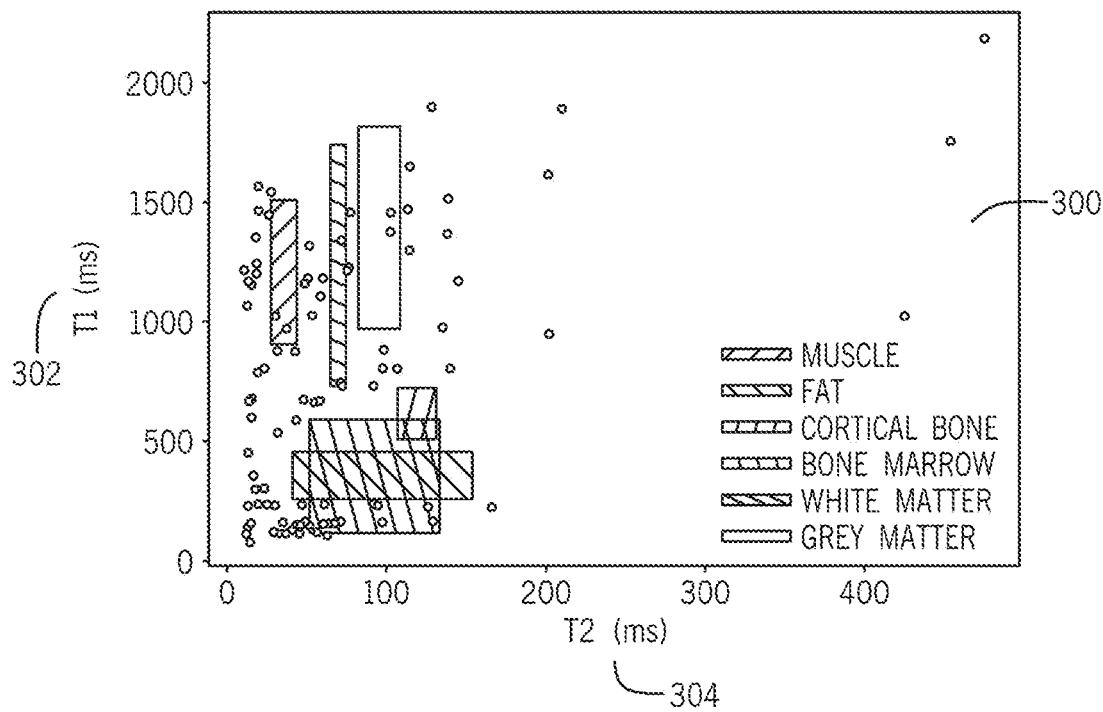
FIG. 3 shows a scatter plot of $T_1$ vs $T_2$ for carrageenan-based samples containing different combinations of Gd, agarose, GMs, and $CaCO_3$ concentrations.
Figure 4:
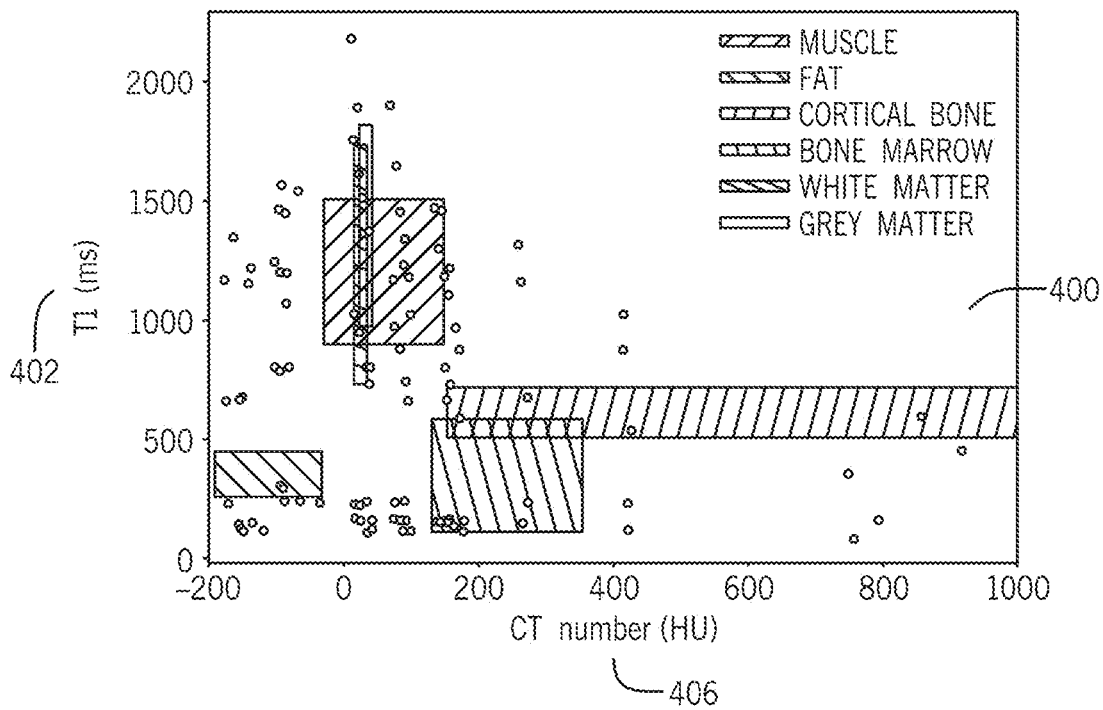
FIG. 4 shows a scatter plot of $T_1$ vs. CT number for carrageenan-based samples containing different combinations of Gd, agarose, GMs, and $CaCO_3$ concentrations.
Figure 5:
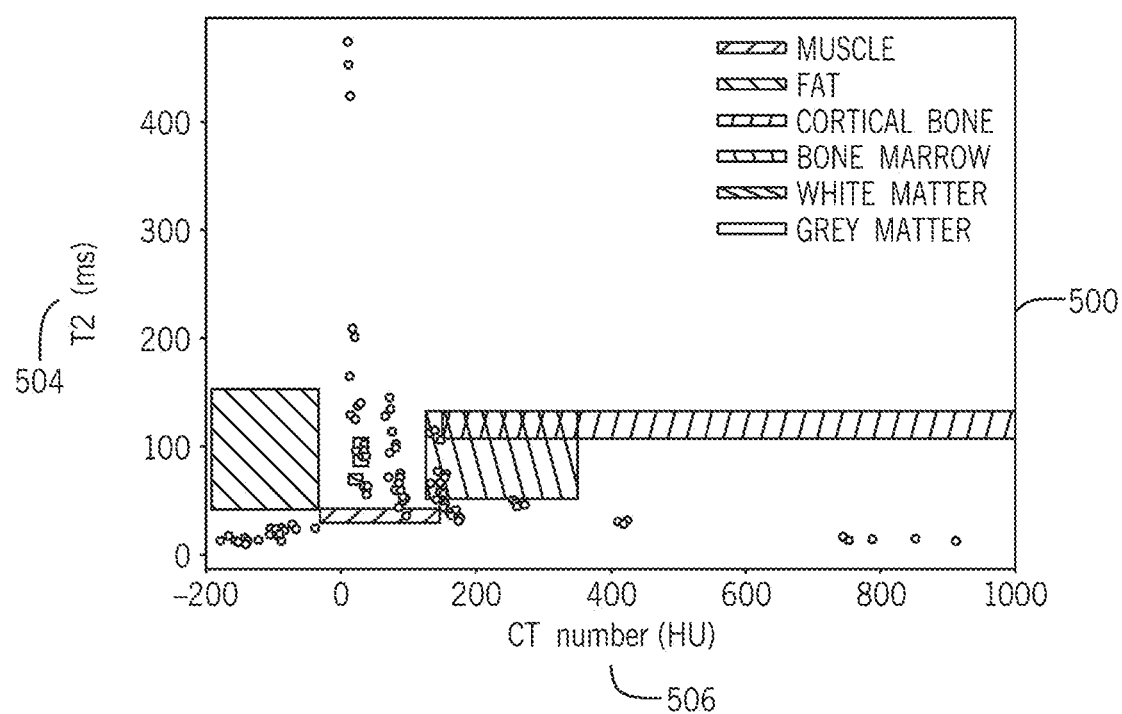
FIG. 5 shows a scatter plot for $T_2$ vs. CT number for carrageenan-based samples containing different combinations of Gd, agarose, GMs, and $CaCO_3$ concentrations.

The validation phantoms samples were used to determine the relationships between $T_1$, $T_2$ and CT number values with concentrations of agarose, Gd contrast, glass microspheres and $CaCO_3$. FIGS. 3, 4 and 5 show all measured $T_1$, $T_2$ and CT number values for each sample. FIG. 3 shows a scatter plot of $T_1$ vs $T_2$ for carrageenan-based samples containing different combinations of Gd, agarose, GMs, and $CaCO_3$ concentrations. The $T_1$ vs $T_2$ results in FIG. 3 show that the concentrations tested for the described system of materials can span a range of $T_1$ values from 82 ms to 2180 ms, and $T_2$ values from 12 ms to 475 ms. FIG. 4 shows a scatter plot of $T_1$ vs. CT number and FIG. 5 shows a scatter plot for $T_2$ vs. CT number for carrageenan-based samples containing different combinations of Gd, agarose, GMs, and $CaCO_3$ concentrations. The $T_1$ vs. CT number results in FIG. 4 and the $T_2$ vs. CT number results in FIG. 5 show that the range of achievable CT numbers is −117 HU to 914 HU. In FIGS. 3, 4, and 5, estimated expected ranges for $T_1$, $T_2$ and CT number for a variety of tissue types including muscle, fat, cortical bone, bone marrow, white matter, and grey matter are shown with cross-hatching. In an example, the expected ranges $T_1$ and $T_2$ regions may be selected based on the minimum and maximum reported measurements from a review of in vivo 3.0T MR, $T_1$ and $T_2$ maps by Bojorquez et al. (J. Z. Bojorquez, S. Bricq, C. Acquitter, F. Brunotte, P. M. Walker, and A. Lalande, Magn. Reson. Imaging 35, 69 (2017)). In addition, the expected CT number ranges may be selected based on literature reported measurements of CT numbers of muscle, fat, cortical bone, bone marrow, white matter and grey matter.

In an embodiment, a multivariate linear regression fit model between $T_1$, $T_2$, and CT number and concentrations of additives was developed to allow the system of materials to be generalized to semi-arbitrary $T_1$, $T_2$ and CT numbers and to mimic various tissue types. The fit model may be used to determine or predict the required additive concentrations to formulate the system of materials to produce a desired set of $T_1$, $T_2$ and CT number values to mimick a particular type of tissue. As described further below, in an example, the $T_1$, $T_2$ relaxation times and CT numbers of a set of diverse tissue types were mimicked to validate the fit model. In an embodiment, the multivariate linear models between $1/T_1$, $1/T_2$ and CT number with respect to the four additives were developed using a python-based Bayesian Ridge regression model. A single predictive model for $T_1$, $T_2$ and CT number may be created by combining each multivariate linear regression:

$$\begin{pmatrix} 1/T_1 \\ 1/T_2 \\ HU \end{pmatrix} = \begin{pmatrix} \alpha_0 & \alpha_{Gd} & \alpha_{Ag} & \alpha_{CaCO_3} & \alpha_{GM} \\ \beta_0 & \beta_{Gd} & \beta_{Ag} & \beta_{CaCO_3} & \beta_{GM} \\ \gamma_0 & \gamma_{Gd} & \gamma_{Ag} & \gamma_{CaCO_3} & \gamma_{GM} \end{pmatrix} \begin{pmatrix} 1 \\ c_{Gd} \\ c_{Ag} \\ c_{CaCO_3} \\ c_{GM} \end{pmatrix} \quad (3)$$

where $(\alpha, \beta, \gamma)_o$ are fit intercepts, $(\alpha, \beta, \gamma)_{Gd,Ag,CaCO3,GM}$ are the fit parameters (or coefficients) for Gd contrast, agarose, $CaCO_3$ or glass microspheres and $c_{Gd,Ag,CaCO3,GM}$ are the input concentrations of each additive. In this example, the fit parameters in equation 3 were established using the sample CT number and $T_1$ and $T_2$ relaxometry measurements. In an embodiment, since this matrix is non-invertible, a method may be developed to predict optimal $c_{Gd,Ag,CaCO3,GM}$. The $c_{Gd,Ag,CaCO3,GM}$ values spanned the tested concentrations to create predicted $1/T_1$, $1/T_2$ and CT number values. The optimal $c_{Gd,Ag,CaCO3,GM}$ concentrations may be obtained by minimizing the difference between in vivo $T_1$, $T_2$ and CT number values:

$$\min\left\{\begin{pmatrix}1/T_1\\1/T_2\\HU\end{pmatrix}_{tissue} - \begin{pmatrix}1/T_1\\1/T_2\\HU\end{pmatrix}_{pred}\right\} \quad (4)$$

An exact solution to the predictive model may be found using a convex optimization solver. However, if an exact solution is not achieved, an optimization method may be used to find the concentrations that minimizes the difference between the predicted and desired $T_1$, $T_2$ and CT numbers.

In an example, the ability of the fit model to correctly estimate the necessary additive concentration was tested for a set of $T_1$, $T_2$, and CT number values representing nine tissue types, specifically, muscle, white matter, gray matter, liver, prostate, glandular breast, adipose tissue, marrow adipose tissue and cortical bone. Target $T_1$, $T_2$ and CT number values were selected from literature reported values of $T_1$, $T_2$ and CT numbers for these tissue types. Samples representing each tissue type was created using the fit model-specified concentrations and imaged under the same conditions as described above with respect to FIGS. 1a, 1b and 2. The measured $T_1$, $T_2$ and CT number values were compared to the corresponding target values for each tissue type. The multivariate fit coefficients (or parameters) $\alpha_{0,Gd,Ag,CaCO3,GM}$ of $1/T_1$ with respect to the four variable additives and calculated using the tissue validation phantom measurements were:

$\alpha_0 = 6.1E-05$ $\alpha_{Gd} = 1.3E-02$ $\alpha_{Ag} = 3.2E-04$ $\alpha_{CaCO3} = 1.4E-04$ $\alpha_{GM} = 1.7E-04$ The multivariate fit coefficients (or parameters) $\beta_{0,Gd,Ag,CaCO3,GM}$ of $1/T_2$ with respect to the four variable additives and calculated using the tissue validation phantom measurements were:

$\beta_0 = 3.4E-03$ $\beta_{Gd} = 1.1E-02$ $\beta_{Ag} = 2.9E-03$ $\beta_{CaCO3} = 1.6E-03$ $\beta_{GM} = 1.4E-02$ The multivariate fit coefficients (or parameters) $\gamma_{0,Gd,Ag,CaCO3,GM}$ of CT number with respect to the four variable additives and calculated using the tissue validation phantom measurements were:

$\gamma_0 = 6.4E+00$ $\gamma_{Gd} = 1.0E+01$ $\gamma_{Ag} = 6.7E+00$ $\gamma_{CaCO3} = 2.7E+01$ $\gamma_{GM} = 3.3E+01$ In this example, additive concentrations predicted by the fit model are shown in Table 1. Table 1 contains the fit model predicted concentrations of Gd contrast, agarose, $CaCO_3$, and glass microspheres required to create the target CT numbers and $T_1$- and $T_2$-relaxation times for each tissue surrogate.

TABLE 1 a) Tissue mimicking material composition

| Tissue type | Gd (umol/50 g) | Agarose (g/50 g) | CaCO3 (g/50 g) | GMs (g/50 g) | Carrageenan (g/50 g) | Water (g/50 g) |
|---|---|---|---|---|---|---|
| Muscle | 0.63 | 0.35 | 2.36 | 1.05 | 1.50 | 44.11 |
| White Matter | 1.81 | 0.44 | 1.65 | 0.61 | 1.50 | 43.99 |
| Gray Matter | 1.39 | 0.35 | 1.66 | 0.40 | 1.50 | 44.7 |
| Liver | 2.07 | 0.59 | 2.26 | 1.46 | 1.50 | 42.12 |
| Prostate | 1.03 | 0.31 | 1.74 | 0.43 | 1.50 | 44.99 |
| Glandular breast | 0.77 | 0.31 | 1.30 | 0.93 | 1.50 | 45.19 |
| Adipose tissue | 11.00 | 0 | 0.00 | 2.50 | 1.50 | 35 |
| Bone Marrow | 7.46 | 0.64 | 3.04 | 0.53 | 1.50 | 36.83 |
| Cortical Bone | 2.00 | 0.90 | 11.00 | 0.00 | 1.50 | 34.6 |

Table 2 shows the measured $T_1$, $T_2$, and CT number values for samples generated with the fit-predicted additive concentrations along with the target values for each tissue for the nine tested tissue types.

TABLE 2

| | 3.0 T T1 (ms) | | 3.0 T T2 (ms) | | CT number (HU) | |
|---|---|---|---|---|---|---|
| Tissue type | In vivo | Tissue Surrogate | In vivo | Tissue Surrogate | In vivo | Tissue Surrogate |
| Muscle | 1420 ± 38 [26] | 1323 ± 138 | 44 ± 9 [27] | 44 ± 3 | 38 (31, 45) [28] | 44 ± 7 |
| White Matter | 1110 ± 40 [29] | 1023 ± 9 | 65 ± 6 [30] | 61 ± 7 | 29 (25, 34) [31] | 47 ± 3 |
| Gray Matter | 1380 ± 59 [32] | 1242 ± 77 | 83 ± 4 [33] | 81 ± 6 | 35 (30, 40) [31] | 41 ± 5 |
| Liver | 809 ± 71 [34] | 917 ± 68 | 34 ± 4 [34] | 37 ± 6 | 24.9 (16.7, 37.2) [35] | 21 ± 1 |

TABLE 2-continued

| | 3.0 T T1 (ms) | | 3.0 T T2 (ms) | | CT number (HU) | |
|---|---|---|---|---|---|---|
| Tissue type | In vivo | Tissue Surrogate | In vivo | Tissue Surrogate | In vivo | Tissue Surrogate |
| Prostate | 1597 ± 42 [34] | 1404 ± 160 | 80 ± 34 [36] | 63 ± 10 | 36 (23, 57) [39] | 41 ± 5 |
| Glandular breast | 1680 ± 180 [37] | 1440 ± 153 | 54 ± 9 [38] | 60 ± 6 | 8 ± 22 [39] | 20 ± 2 |
| Adipose tissue | 366 ± 75 [38] | 388 ± 54 | 68 ± 4 [34] | 42 ± 8 | −95 ± 9 [40] | −50 ± 89 |
| Bone Marrow | 381 ± 8 [41] | 445 ± 6 | 52 ± 1 [41] | 58 ± 4 | 77 ± 75 [43] | 76 ± 8 |
| Cortical Bone | 716 ± 115 [42] | 780 ± 95 | 120 ± 13 [42] | 39 ± 18 | 345 ± 21 [44] | 347 ± 5 |

In this example, the nine tissue types were formulated using the system of materials three times. The standard deviation for the tissue-mimicking materials are based on the standard deviation of the mean region of interest measurements from the three repeated samples. The mean error between the fit-model predicted and the measured $T_1$, $T_2$ and CT number values for the nine tested tissue types was 123±102 ms, 15±18 ms and 7±6 HU, respectively. For the nine tested tissue types, the multivariate fit model yielded a mean absolute percentage error between the fit-model-predicted and the measured CT number and $T_1$- and $T_2$-relaxation tissue of 23%, 11% and 19% respectively.

In an embodiment, to mimic adipose tissue using the system of materials additional GMs may be required to correctly mimic the $T_2$ characteristics of adipose. The addition of GMs may degrade the $T_2$ relaxation time. To mitigate this, in an embodiment the glass microspheres may be pretreated with hemp oil prior to mixing. Mixing the glass microspheres with small amounts of oil increased the $T_2$ relaxation time and stabilized the glass microsphere powder making it easier to process. Hemp oil has a measured $T_2$ relaxation time at 180±2 ms. In another embodiment, preservative, such as sodium azide or thimerosal may be included in the system of materials to preserve the carrageenan-based or agarose gel-based materials. In an embodiment, the disclosed system of materials may be used to mimic different types of adipose tissue such as brown adipose tissue and tumors.

As mentioned above, the disclosed system of materials may be used to create a realistic multimodality MR-CT imaging phantom for anatomical sites in the human body. For example, the system of materials may be cast and formed in the shape of organs to create anthropomorphic phantoms. The system of materials may be disposed within a housing (e.g., polyurethane). FIGS. 6a-6e illustrate an example phantom and a design and fabrication process in accordance with an embodiment. The example phantom shown in FIGS. 6b-6e is a phantom of the male pelvic anatomy. While the following description will refer to the multimodality pelvic phantom, it should be understood that the system of materials and the fabrication process described may be used to create a phantom of any anatomical structure or region.

Figure 6A:
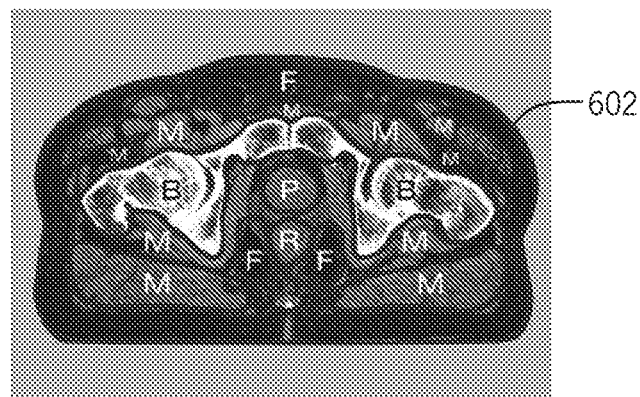
FIG. 6a shows an example segmented CT image of a patient used in a design and fabrication process for a multimodality phantom in accordance with an embodiment.

FIG. 6a shows an example segmented CT image of a patient used in a design and fabrication process for a multimodality phantom in accordance with an embodiment. The reference CT image 602 is used as a template for the phantom design. For a pelvic phantom, the reference CT image may be, for example, an image of a typical prostate cancer patient. To design the pelvic phantom, major anatomical structures such as the gross musculature (M), adipose tissue (F), prostate (P), rectum (R) and pelvic bone (B) are segmented on the reference patient CT image 602. Other structures, such as the bladder and penile bulb may also be segmented. The tissue segmentation may be performed using known methods. The segmented image 602 provides a template of the anatomy with thin boundaries separating tissue types. The segmented or contoured gross musculature, prostate, rectum, bladder, penile bulb, pelvic bones and adipose tissue are used to define rigid tissue compartments in the phantom structure (or housing). In an embodiment, the resultant contours were expanded to create, for example, 2 mm thick walls to create the rigid tissue compartments that separate the tissue types in the phantom housing. The rigid tissue compartment contours may be represented as a mesh using, for example, computer software. In an embodiment, the rigid tissue compartment mesh may then be smoothed using Laplacian smoothing without surface modification to remove self-intersecting vertices and simplify generation of a structure-defining triangular mesh. The smoothed rigid compartment mesh may then be converted into a solid structure using a computer aided design program, such as, for example, AutoCAD.

Figure 6B:
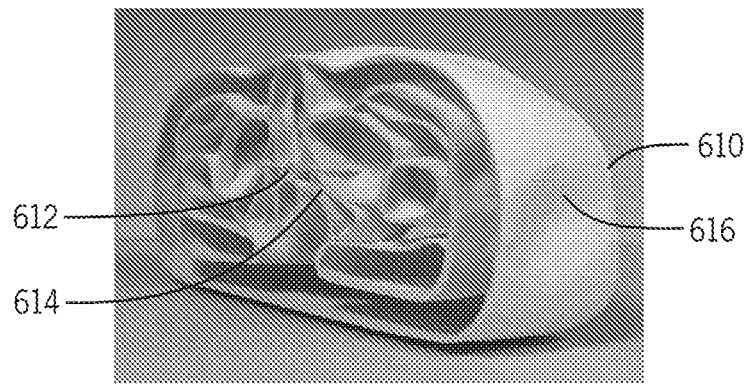
FIG. 6b shows a first section of a housing for a multimodality phantom in accordance with an embodiment.
Figure 6C:
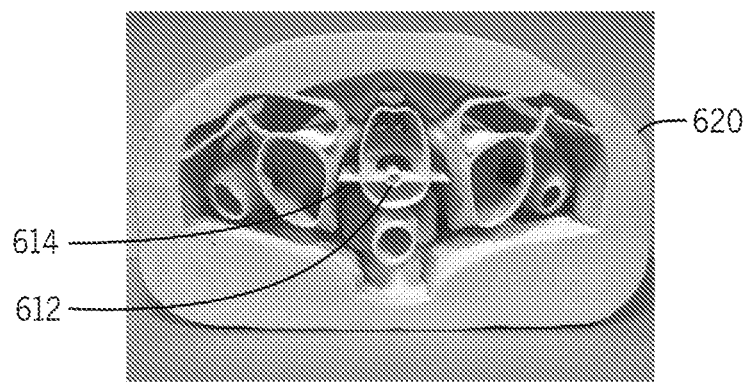
FIG. 6c shows a second section of a multimodality phantom in accordance with an embodiment.
Figure 6D:
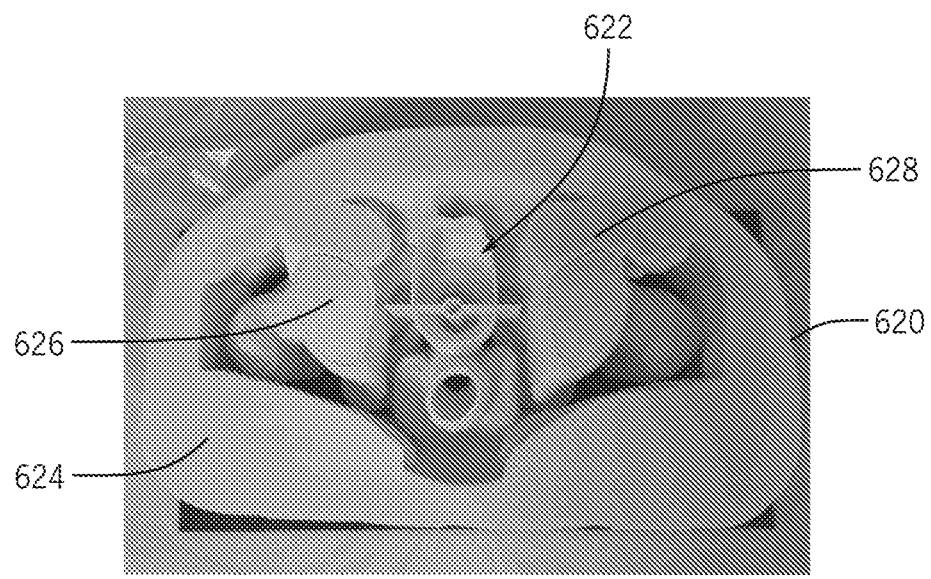
FIG. 6d shows the second section of the multimodality phantom partially filled in with a system of materials configured to mimic soft tissue and bone in accordance with an embodiment.
Figure 6E:
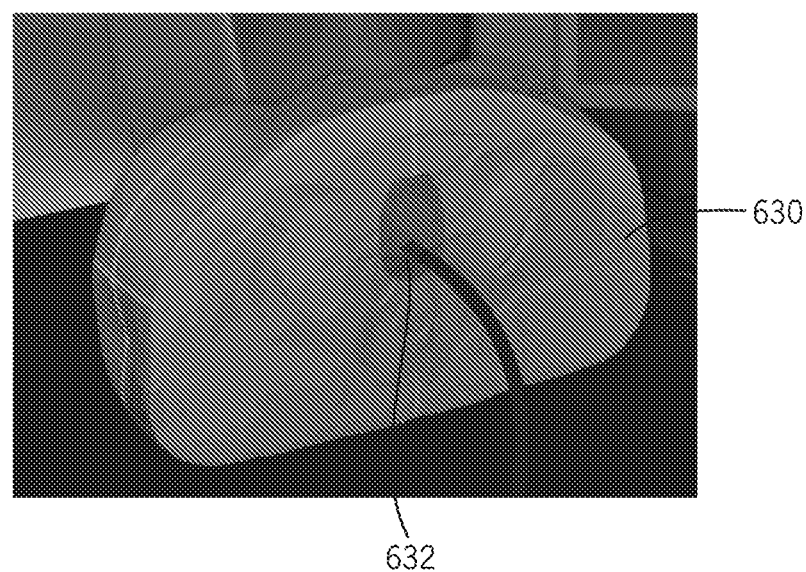
FIG. 6e shows a completed multimodality phantom with an inserted ionization chamber in accordance with an embodiment.

In an embodiment, the structure (or housing) of the phantom may be constructed using 3D printing and based on the computer aided design model. FIG. 6b shows a first section of a housing for a multimodality phantom in accordance with an embodiment and FIG. 6c shows a second section of a multimodality phantom in accordance with an embodiment. In one embodiment, the phantom housing or each section of the housing may be 3D-printed as a single piece. FIG. 6b shows a front section 610 of the phantom housing and FIG. 6c shows a back section 620 of the phantom housing. FIGS. 6b and 6c show the various rigidly separated compartments that conform to the pelvic anatomy. In an embodiment, the phantom structure or housing includes a slot 614 to allow insertion of a dosimeter and includes a plurality of adapters 612 to allow for the placement of one or more radiation measurement devices such as an ion chamber and radiochromic film. The structure may also include alignment crosshair indentations 616 and a flat base to facilitate reproducible phantom positioning. The tissue compartments may be filled with the system of materials described above (e.g., the carrageenan-based system of materials) that is designed to mimic the $T_1$ and $T_2$ relaxation times and electron densities of the corresponding soft tissue or bone. In an embodiment, the system of materials corresponding to a particular soft tissue or bone may be poured into the rigid compartment corresponding to the particular sift tissue or bone. In an example, the system of materials may be poured into the phantom housing in layers allowing the previous layer to solidify. FIG. 6d shows the second section of the multimodality phantom partially filled in with a system of materials configured to mimic soft tissue and bone in accordance with an embodiment. In FIG. 6d, the compartments of the back section 620 of the housing corresponding to adipose tissue 624, pelvic bone 626 and muscle 628 are each filled with a system of materials. A bladder compartment 622 is labelled for reference. In an embodiment, a closure lid may be provided (e.g., the lid may also be 3D-printed) to protect the internal components of the phantom. FIG. 6e shows a completed multimodality phantom 630 with an inserted ionization chamber 632 in accordance with an embodiment. In an embodiment, the phantom could be 3D-printed with deformable interfaces, which could increase its utility for MR-guided radiotherapy applications. For example, a dual extruder 3D-printer containing a deformable filament (such as thermoplastic polyurethane) and a solid-at-room temperature filament (such as PLA). Using a dual extruder 3D-printer, a tissue mimicking MR-CT phantom with a mixture of solid and deformable walls could be fabricated and filled with the deformable carrageenan-based materials described above. In another embodiment, the system of materials and the method for design and fabrication of the phantom may allow for modular MR/CT phantoms to be developed potentially incorporating many deformable organs.

Table 3 summarizes example material mixtures used to create mimics of skeletal muscle, prostate, trabecular bone, adipose tissue or urinary bladder. In this example, a carrageenan-based water surrogate material was developed for urinary bladder, the gross musculature and penile bulb structures were filled with muscle-mimicking material and the prostate and rectum structures were filled with the prostate-mimicking material. In an embodiment, the pelvic bone is treated as a single homogeneous material. In another embodiment, the pelvic bone is treated as being heterogeneous.

the inversion time (TI) was varied from 25 ms to 200 ms in 50 ms steps. Images were acquired with an echo train length of 5, no signal averaging, and no parallel imaging. A $T_1$ map was generated by performing a voxel-wise fit to the observed signal intensity using:

$$M_{z,TE_i} = M_0(1 - 2e^{-TI/T1} - e^{-TR/T1}) \qquad (5)$$

where $M_0$ is the initial magnetization vector magnitude. $T_2$ measurements were acquired using spin echo images using a TSE sequence with a constant TR at 4000 ms and TE values 25, 50, 62, 75, 87, 107, 167, and 262 ms. Images were acquired with an echo train length of 25, no signal averaging and without parallel imaging. $T_2$ maps were generated by performing a voxel-wise fit using:

$$M_{TE_i} = M_0\left(e^{\frac{TE_i}{T_2}}\right) + c \qquad (6)$$

where c is a noise offset variable. In this example, MR and CT tissue imaging characteristics were quantified by measuring the $T_1$ and $T_2$ relaxation times and CT numbers of prostate, skeletal muscle, pelvic bone, and adipose tissue mimics in the phantom via region-of-interest (ROI) analysis and compared to in vivo literature measurements. ROIs were placed in homogeneous regions of the urinary bladder, pelvic bone, adipose tissue, prostate and muscle mimicking materials. The same ROIs were used across all image sets.

TABLE 3

Mixtures to create 100 g tissue mimicking material

| Tissue type | Gd solution (g) | Agarose (g) | CaCO3 (g) | GMs (g) | Carrageenan (g) | Water (g) |
|---|---|---|---|---|---|---|
| Muscle | $1.2 \times 10^{-3}$ | $7.0 \times 10^{-1}$ | 4.7 | 2.0 | 3.0 | 89.5 |
| Prostate | $2.0 \times 10^{-3}$ | $6.2 \times 10^{-1}$ | 3.5 | $8.7 \times 10^{-1}$ | 3.0 | 92.0 |
| Pelvic Bone | $3.9 \times 10^{-3}$ | 1.8 | 22.0 | 0 | 3.0 | 73.2 |
| Adipose Tissue | $1.5 \times 10^{-2}$ | 0 | 0 | $8.0 \times 10^{-1}$ | 3.0 | 96.2 |
| Urinary Bladder | 0 | 0 | 0 | 0 | 2.0 | 98.0 |

Figure 7:
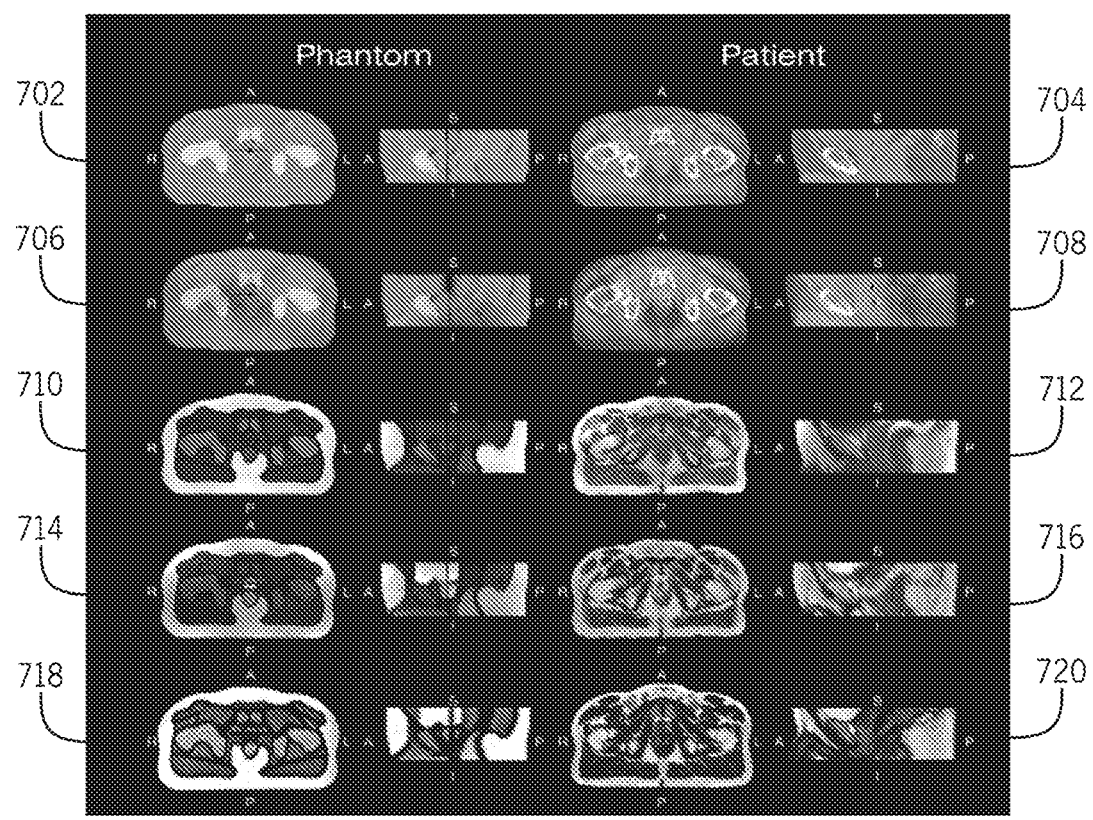
FIG. 7 shows axial and sagittal images of a multimodality phantom and a patient in accordance with an embodiment.

In an example, the phantom described above with respect to FIGS. 6b-6e was evaluated by acquiring CT and MR images of the phantom using the CT and MR images to compare the phantom $T_1$ and $T_2$ relaxation times and electron densities to literature-reported values for human tissue. The MR and CT tissue imaging characteristics were quantified using $T_1$ and $T_2$ mapping and CT number measurements. In this example, CT images were acquired on a 20-slice single source CT with 120 kVp and 400 mA. $T_1$- and $T_2$-weighted Turbo Spin Echo (TSE) MR images were acquired on 1.5T and 3.0T MR systems. All measurements were performed at 20-22° C. In addition, a 0.35T True Fast Imaging with Steady State Free Precession (TRUFI) MR image was acquired on a real-time 0.35T MR-guided radiation therapy system. The TRUFI sequence is a type of bSSFP sequence that yields images with $T_1/T_2$-weighted contrast. TRUFI images were acquired with a 60° flip angle, TR=3.37 ms, TE=145 ms, an echo train length of 1 and no signal averaging. $T_1$ mapping measurements were done using an inversion-recovery TSE sequence with 180-degree refocusing pulses. The echo time (TE) and repetition time (TR) were fixed at 12 ms and 15,000 ms, respectively, and FIG. 7 shows axial and sagittal images of a multimodality phantom and a patient in accordance with an embodiment. FIG. 7 shows a comparison of axial and sagittal CT images of the phantom 702 and the example patient 704, axial and sagittal cone beam (CBCT) images of the phantom 706 and example patient 708, axial and sagittal 3.0T $T_1$-weighted TSE MR images of the phantom 710 and the example patient 712, axial and sagittal 3.0T $T_2$-weighted TSE MR images of the phantom 714 and the example patient 716 and axial and sagittal 0.35T TRUFI MR images of the phantom 718 and the example patient 720. In FIG. 7, the anterior-posterior (AP), left-right (LR) and superior-inferior (SI) directions are labelled for reference. The described system of tissue-mimicking materials does not exhibit shadowing artifacts allowing the generation of a relatively artifact free $T_1$- or $T_2$-weighted MR images. A comparison between the measured CT number values for the phantom and the in vivo literature reported CT numbers for pelvic bone, adipose tissue, muscle and prostate tissues are reported in Table 4a. A comparison between the measured $T_1$ and $T_2$ relaxation times for the phantom and the in vivo literature reported $T_1$ and $T_2$ relaxation times for pelvic bone, adipose tissue, muscle and prostate tissues for measurements at 1.5T and 3.0T are reported in Tables 4b and 4c.

TABLES 4a-4c

| | Tissue Type | Pelvic Bone | Adipose Tissue | Muscle | Prostate |
|---|---|---|---|---|---|
| | | a. | | | |
| CT | $CTN_{phantom}$ (HU) | 340 ± 29 | −11 ± 8 | 39 ± 10 | 35 ± 11 |
| | $CTN_{1.5\,TsCT}$ (HU) | 376 ± 35 | −96 ± 4 | 36 ± 3 | 36 ± 9 |
| | $CTN_{3.0\,TsCT}$ (HU) | 394 ± 35 | −97 ± 4 | 37 ± 2 | 37 ± 10 |
| | $CTN_{literature}$ (HU) | 345 ± 21 [31] | −95 ± 9 [32] | 38 [33] | 36 [34] |
| | | b. | | | |
| 1.5 T | $T1_{phantom}$ (ms) | 547 ± 17 | 285 ± 3 | 1014 ± 9 | 1314 ± 33 |
| | $T1_{literature}$ (ms) | 549 ± 42 [35] | 296 ± 12.9 [36] | 1042 ± 163 [39] | 1317 ± 35 [35] |
| | $T2_{phantom}$ (ms) | 49 ± 4 | 165 ± 6 | 53 ± 10 | 88 ± 0 |
| | $T2_{literature}$ (ms) | 47 ± 2 [35] | 151 ± 25 [40] | 52 ± 3 [41] | 89 ± 12 [35] |
| | | c. | | | |
| 3.0 T | $T1_{phantom}$ (ms) | 597 ± 10 | 353 ± 8 | 1124 ± 30 | 1278 ± 32 |
| | $T1_{literature}$ (ms) | 586 ± 73 [35] | 367 ± 8 [36] | 1100 ± 78 [37] | 1400 ± 278 [38] |
| | $T2_{phantom}$ (ms) | 50 ± 5 | 71 ± 3 | 40 ± 2 | 85 ± 3 |
| | $T2_{literature}$ (ms) | 49 ± 8 [35] | 68 ± 4 [35] | 40 ± 3 [29] | 80 ± 34 [29] |

The CT numbers from synthetic CT (sCT) images derived from 1.5T- and 3.0T MR images of the phantom are presented in Tables 4a-4c for reference. In this example, the measured CT number for the urinary bladder-mimicking material was 11±8.5 HU. The $T_1$ and $T_2$ relaxation times, measured at 1.5T, for the urinary bladder mimicking material were 188±30 ms and 377±43 ms, respectively. The maximum absolute differences in CT number between in vivo tissues and phantom tissue-mimicking materials was less than 2.8% for prostate, pelvic bone, and muscle. The mean and maximum absolute differences in $T_1$ and $T_2$ relaxation times at 1.5T between in vivo tissues and phantom tissue-mimicking materials was 3.0% and 9.3%, respectively. The mean and maximum absolute differences in $T_1$ and $T_2$ relaxation times at 3.0T between in vivo tissues and phantom tissue-mimicking materials was 3.7% and 8.7%, respectively. As mentioned above, ROI analysis was also performed to assess MR and CT contrast uniformity within the phantom. ROIs were drawn in the first and second slices in the phantom for skeletal muscle, trabecular bone, and adipose tissues. The mean signal change for skeletal muscle, trabecular bone, and adipose tissue was less than 1.9%, 2.2%, and 0.5% in 3.0T $T_1/T_2$ TSE MR images. The mean CT number difference for skeletal muscle, trabecular bone, and adipose tissue 0.1%, 0.1%, and 1%, respectively. To examine the reproducibility of the phantom materials, the phantom was built twice to evaluate the changes in $T_1/T_2$-relaxation times and CT numbers. The mean $T_1$- and $T_2$-relaxation times and CT number differences across all simulated tissue types was 40 ms, 12 ms, and 11 HU, respectively.

Figure 8:
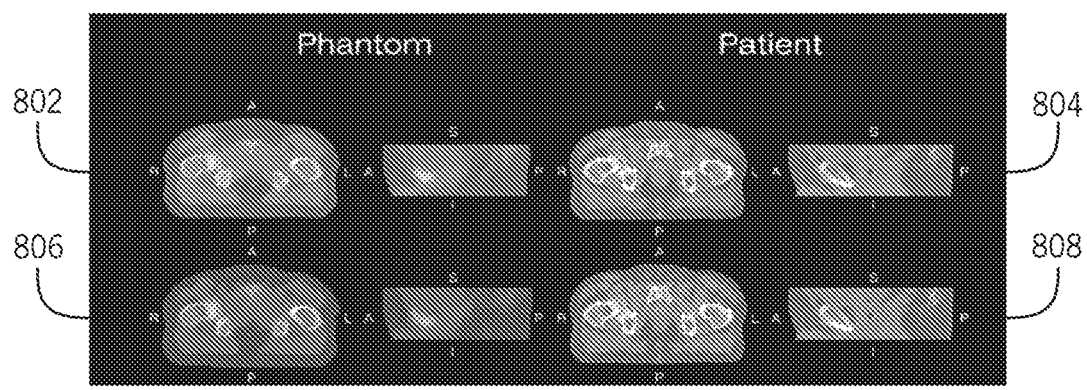
FIG. 8 shows axial and sagittal 1.5T and 3.0T derived sCT images of a multimodality phantom and reference patient images in accordance with an embodiment.

In another example, the phantom described above with respect to FIGS. 6b-6e was evaluated by using the phantom for end-to-end testing of an MR-only treatment simulation and planning workflow. In particular, in this example the end-to-end testing included evaluation of synthetic CT (sCT) images generated using MR images of the phantom (phantom-based sCT images), dosimetric accuracy, and alignment accuracy of Stereotactic Body Radiation Therapy (SBRT) Volumetric-modulated Arc Therapy (VMAT) and 7-field Intensity-Modulated Radiation Therapy (IMRT) prostate plans. The MR-only plans were created using phantom-based sCT images and the end-to-end testing was performed by comparing the planned and delivered dose differences between the MR-only plans and CT-based plans. In this example, sCT images were created using a statistical decomposition algorithm that takes a $T_2$-weighted MR image as input. FIG. 8 shows axial and sagittal 1.5T/3.0T derived sCT images of a multimodality phantom and reference patient images in accordance with an embodiment. FIG. 8 shows a comparison of axial and sagittal sCT images generated from 1.5T images of the phantom 802 and example patient CT images 804 and a comparison of axial and sagittal sCT images generated from 3.0T images of the phantom 806 and example patient CT images 808. The phantom-based sCT images were used for dose calculation during treatment planning of VMAT and 7-field IMRT prostate plans. For treatment planning, the femoral heads, rectum and bladder of the phantom were contoured as Organs-At-Risk (OAR), and the prostate was contoured as a target on the image. The Planning Target Volume (PTV) was defined by applying a 3 mm margin to the prostate. The plan for both treatment types (VMAT and IMRT) were normalized for 98% PTV coverage. The MR-only VMAT and IMRT plans were delivered to the phantom on a linear accelerator and radiosurgery treatment system. During treatment delivery, a 0.3 cc ion chamber and radiochromic film were placed in the phantom and used to measure the delivered dose (e.g., the absolute dose and spatial dose distribution).

Doses calculated on CT images of the phantom and the phantom-based sCT images were compared using common dose volume histogram (DVH) metrics. Gamma analysis was performed using the film measurements at 3%/3 mm and a 30% dose threshold. The gamma pass rates and measured point dose differences were computed using the planned doses on the CT image as a reference. In this example, film analysis resulted in a 99.7% gamma-pass-rate (3%, 3.0 mm) for both the VMAT and IMRT plans. The measured percent point dose differences and 3%/3 mm gamma pass rates for the delivered IMRT were 0.36% and 99.7%±0.5%, respectively. The measured percent point dose differences and 3%/3 mm gamma pass rates for the delivered VMAT were 1.67% and 99.7%±0.6%, respectively. The ion chamber measured dose discrepancies at the isocenter were 0.36% and 1.67% for the IMRT and VMAT plans, respectively. The differences in PTV D97 and D95% between plans calculated on the CT images of the phantom and the 1.5T/3.0T derived phantom-based sCT images were under 3%. The mean-absolute-error (MAE) and the bone Dice Similarity Coefficient (DSC) were compared between the 1.5T/3.0T derived phantom-based sCT images and the CT images of the patient. sCT and plan dose differences were evaluated for a 6 MV, 180 cGy, 7-field IMRT and 800 cGy SBRT VMAT plan. The MAE's between the 1.5T/3.0T sCTs and corresponding CTs of the phantom were 30 and 32 HU, respectively. The bone DSC scores between the 1.5T/3.0T sCTs and corresponding CTs of the phantom were 0.83 and 0.81, respectively. A comparison of the OAR and PTV dose differences for the VMAT and IMRT doses calculated on the 1.5T/3.0T sCT, and CT images of the phantom for this example are shown in Table 5. In Table 5, the OAR volume dose metrics are indicated as the volume that receives equal or more than the reported percentage of the prescription dose. The largest PTV D95% difference between plans calculated on the sCT and CT images was 2.9%.

TABLE 5

| | IMRT 1.5 T sCT-CT | IMRT 3.0 T sCT-CT | VMAT 1.5 T sCT-CT | VMAT 3.0 T sCT-CT |
|---|---|---|---|---|
| PTV D98% (%) | 2.4 | 1.6 | 2.8 | 1.9 |
| PTV D95% (%) | 2.6 | 1.8 | 2.9 | 2 |
| Rectum V50% (cc) | 0.3 | 0.2 | 0.3 | 0.3 |
| Rectum V70% (cc) | 1.2 | 1.2 | 1.2 | 1.2 |
| Bladder V65% (cc) | 0.6 | 0.2 | 0.8 | 1.1 |
| Bladder V80% (cc) | 0.6 | 0.2 | 0.7 | 0.9 |
| Left Femur $D_{max}$ (%) | 0.4 | 0.4 | 2.1 | 2 |
| Right Femur $D_{max}$ (%) | 0.6 | 0.5 | 0.1 | 0.1 |

In this example, alignment differences between MR-only and CT images were quantified and sCT image quality test were performed. DRR images were derived from the CT images, sCT images, and a set of projection X-ray images of the phantom were acquired. Alignment differences were quantified using sCT/CT-to-CBCT and DRR-to-X-ray pair alignments. Alignments were performed using translational bone-based shifts. The alignment difference, $\Delta P_{x,y,z}^{sCT,CT}$, between sCT/CT-to-CBCT registrations was evaluated using:

$$\Delta P_{x,y,z}^{sCT,CT} = |P_{x,y,z}^{sCT,CBCT} - P_{x,y,z}^{CT,CBCT}| \quad (7)$$

where $P_{x,y,z}^{CT,CBCT}$ is the alignment resulting from registration between the CT and CBCT images and $P_{x,y,z}^{sCT,CBCT}$ is the alignment resulting from registration between the sCT and CBCT images. The alignment difference, $\Delta Q_{x,y,z}^{sCT, CT\,DRR}$, between DRR-to-X-ray pair alignments was evaluated using:

$$\Delta Q_{x,y,z}^{sCT,CT\,DRR} = |Q_{x,y,z}^{sCT\,DRR,X\text{-}ray} - Q_{x,y,z}^{CT\,DRR,X\text{-}ray}| \quad (8)$$

where $Q_{x,y,z}^{sCT\,DRR,X\text{-}ray}$ and $Q_{x,y,z}^{CT\,DRR,X\text{-}ray}$ are the alignments resulting from registration of the orthogonal X-ray image pairs to sCT DRRs and CT DRRs respectively. In this example, the phantom was setup four times on a treatment couch of the linear accelerator and radiosurgery treatment system. CBCT and X-ray image pairs were acquired for each setup.

Alignment discrepancies between the 1.5T/3.0T sCT to CT and 1.5T/3.0T sCT DRRs to kV/kV orthogonal pair images are shown in Table 6.

DRR images generated from the planning CT images. In Table 6, alignment discrepancies are shown in the AP, LR and SI directions. In this example, these results are based on four separate phantom setups.

Figure 9:
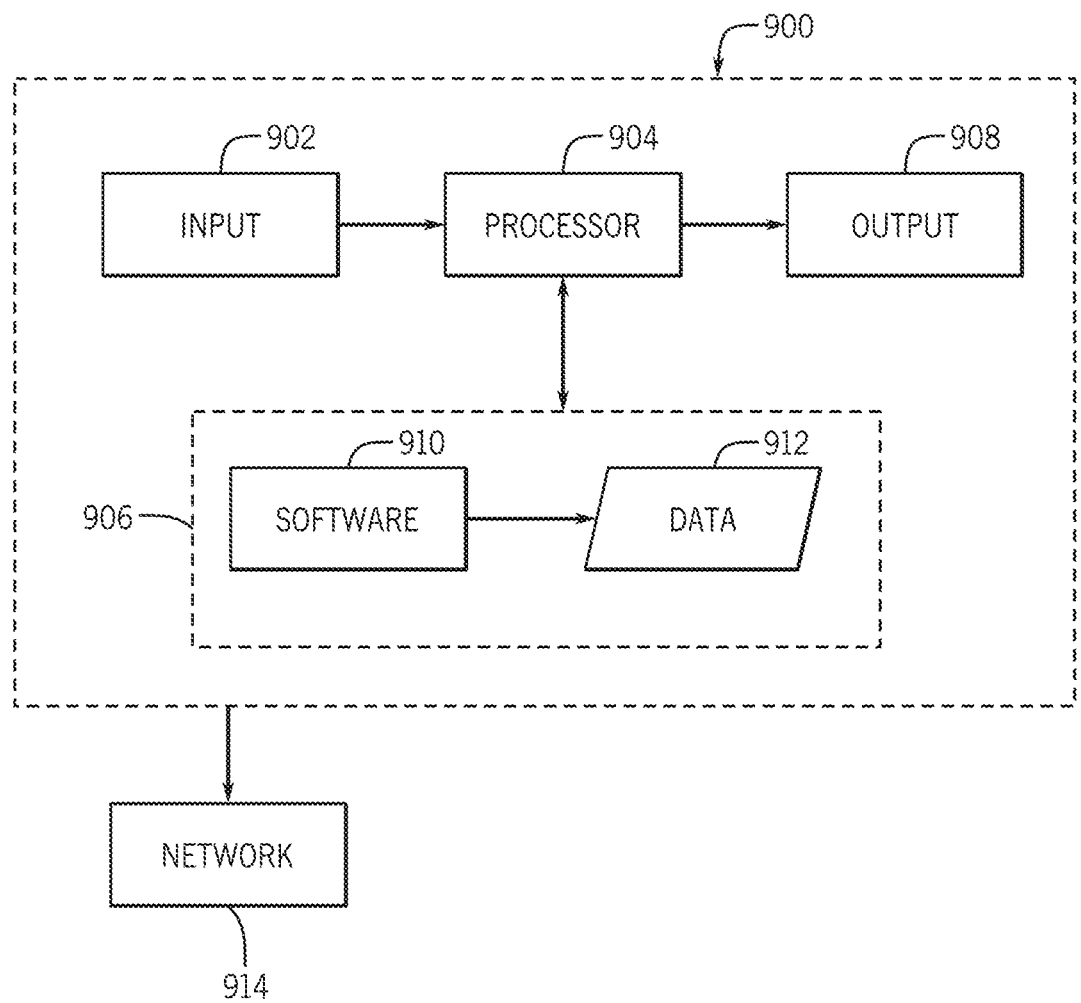
FIG. 9 is a block diagram of an example computer system in accordance with an embodiment.

FIG. 9 is a block diagram of an example computer system in accordance with an embodiment. Computer system 900 may be used to implement various methods described herein. The computer system 900 generally includes an input 902, at least one hardware processor 904, a memory 906, and an output 908. Thus, the computer system 900 is generally implemented with a hardware processor 904 and a memory 906. In some embodiments, the computer system 900 may be a workstation, a notebook computer, a tablet device, a mobile device, a multimedia device, a network server, a mainframe, one or more controller, one or more microcontrollers, or any other general-purpose or application-specific computing device.

The computer system 900 may operate autonomously or semi-autonomously, or may read executable software instructions from memory 906 or a computer-readable medium (e.g., hard drive a CD-RIOM, flash memory), or may receive instructions via the input from a user, or any other source logically connected to a computer or device, such as another networked computer or server. Thus, in some embodiments, the computer system 900 can also include any suitable device for reading computer-readable storage media. In general, the computer system 900 may be programmed or otherwise configured to implement the methods and algorithms described in the present disclosure.

The input 902 may take any suitable shape or form, as desired, for operation of the computer system 900, including the ability for selecting, entering, or otherwise specifying parameters consistent with performing tasks, processing data, or operating the computer system 900. In some aspects, the input 902 may be configured to receive data, such as imaging data, measurement data, and clinical data. In addition, the input 902 may also be configured to receive any other data or information considered useful for implementing the methods described above. Among the processing tasks for operating the computer system 900, the one or more hardware processors 904 may also be configured to carry out any number of post-processing steps on data received by way of the input 902.

The memory 906 may contain software 910 and data 912, such as imaging data, clinical data and molecular data, and may be configured for storage and retrieval of processed information, instructions, and data to be processed by the one or more hardware processors 904. In some aspects, the software 910 may contain instructions directed to implementing one or more machine learning algorithms with a hardware processor 904 and memory 906. In addition, the output 908 may take any form, as desired, and may be configured for displaying images, patient information, parameter maps, and reports, in addition to other desired

TABLE 6

| | DRR to X-ray pair | | | CT to CBCT | | |
|---|---|---|---|---|---|---|
| | $\Delta Q_{LR}^{sCT,\,CT\,DRR}$ (mm) | $\Delta Q_{AP}^{sCT,\,CT\,DRR}$ (mm) | $\Delta Q_{SI}^{sCT,\,CT\,DRR}$ (mm) | $\Delta Q_{LR}^{sCT,\,CT\,DRR}$ (mm) | $\Delta Q_{AP}^{sCT,\,CT\,DRR}$ (mm) | $\Delta Q_{SI}^{sCT,\,CT\,DRR}$ (mm) |
| 1.5 T sCT | 0.7 ± 0.5 | 0.8 ± 0.4 | 0.7 ± 0.9 | 0.1 ± 0.2 | 0.6 ± 0.4 | 0.7 ± 1.1 |
| 3.0 T sCT | 0.6 ± 0.5 | 0.3 ± 0.3 | 0.8 ± 0.5 | 0.2 ± 0.2 | 0.8 ± 0.8 | 0.7 ± 0.5 |

Table 6 summarizes the results of the mean alignment discrepancies between orthogonal X-ray image pairs and, information. Computer system 900 may also be coupled to a network 914 using a communication link 916. The communication link 916 may be a wireless connection, cable connection, or any other means capable of allowing communication to occur between computer system 900 and network 914.

Computer-executable instructions for the design, fabrication, and applications of the phantom according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access The present invention has been described in terms of one or more preferred embodiments, and it should be appreciated that many equivalents, alternatives, variations, and modifications, aside from those expressly states, are possible and within the scope of the invention.

The invention claimed is:

1. A multimodality phantom apparatus comprising:
   a housing; and
   a system of materials disposed within the housing and comprising:
   a first amount of a base material;
   a second amount of glass microspheres;
   a third amount of $CaCO_3$;
   a fourth amount of gadolinium contrast and
   a fifth amount of agarose;
   wherein the second amount of glass microspheres, third amount of $CaCO_3$, fourth amount of gadolinium contrast, and fifth amount of agarose are determined by optimization of a regression model over parameters $T_1$, $T_2$, and CT number.

2. The multimodality phantom apparatus according to claim 1, where the housing has a shape of a human organ.

3. The multimodality phantom apparatus according to claim 1, wherein the glass microspheres are configured to control electron density.

4. The multimodality phantom apparatus according to claim 3, wherein the glass microspheres are configured to diminish CT number values.

5. The multimodality phantom apparatus according to claim 1, wherein the $CaCO_3$ is configured to control electron density.

6. The multimodality phantom apparatus according to claim 5, wherein the $CaCO_3$ is configured to increase CT number values.

7. The multimodality phantom apparatus according to claim 1, wherein the gadolinium contrast is configured to control $T_1$ behavior.

8. The multimodality phantom apparatus according to claim 1, wherein the agarose is configured to control $T_2$ behavior.

9. The multimodality phantom apparatus according to claim 1, wherein the apparatus is configured for use with MR imaging and CT imaging.

10. The multimodal phantom apparatus according to claim 1, wherein the base material is a carrageenan based gelatinizer.

11. A multimodality phantom comprising:
    a housing having a plurality of compartments and at least one slot, the slot configured to receive a dosimeter; and
    a system of materials disposed within at least one compartment in the plurality of compartments, the system of materials comprising:
    a first amount of a base material;
    a second amount of glass microspheres;
    a third amount of $CaCO_3$;
    a fourth amount of gadolinium contrast and
    a fifth amount of agarose;
    wherein the second amount of glass microspheres, third amount of $CaCO_3$, fourth amount of gadolinium contrast, and fifth amount of agarose are determined by optimization of a regression model over parameters $T_1$, $T_2$, and CT number.

12. The multimodality phantom according to claim 11, wherein at least one compartment has a shape of a human organ.

13. The multimodality phantom according to claim 11, wherein the phantom is configured for use with MR imaging and CT imaging.

14. The multimodality phantom according to claim 11, wherein the at least one slot is further configured to house at least one radiation measurement device.

15. The multimodality phantom according to claim 11, wherein the phantom is configured for use with MR-based radiotherapy.

16. The multimodality phantom according to claim 11, wherein the phantom is configured for use to test synthetic CT generation.

17. The multimodality phantom according to claim 11, wherein the phantom is configured for use with MR-CT imaging applications.

18. The multimodality phantom according to claim 11, wherein the system of materials is formed to have a shape of a human organ.

19. The multimodality phantom according to claim 11, wherein at least one compartment of the plurality of compartments has at least one rigid wall.

20. The multimodality phantom according to claim 11, wherein the at least one compartment of the plurality of compartments has at least one deformable wall.

* * * * *